United States Patent [19]

Koppel

[11] 4,042,585
[45] Aug. 16, 1977

[54] PROCESS FOR PREPARATION OF 3-HALOMETHYLCEPHEMS

[75] Inventor: Gary A. Koppel, Indianapolis, Ind.

[73] Assignee: Eli Lilly and Company, Indianapolis, Ind.

[21] Appl. No.: 669,365

[22] Filed: Mar. 22, 1976

[51] Int. Cl.² .................. C07D 501/04; A61K 31/545
[52] U.S. Cl. ...................................... 544/22; 424/246; 260/239.3 B; 260/239.1; 544/16; 544/21
[58] Field of Search .......................... 260/243 C, 239.3

[56] References Cited

U.S. PATENT DOCUMENTS

| 3,637,678 | 1/1972 | Webber et al. | 260/243 C |
| 3,637,678 | 1/1972 | Webber et al. | 260/243 C |
| 3,658,799 | 4/1972 | Eardley et al. | 260/243 C |
| 3,705,897 | 12/1972 | Murphy | 260/243 C |
| 3,705,897 | 12/1972 | Murphy | 260/243 C |

FOREIGN PATENT DOCUMENTS 1,407,348   9/1975   United Kingdom ............. 260/243 C

OTHER PUBLICATIONS

Koppel et al., JACS vol. 95, 2403 (1973).
Karady et al., Tetrahedron Letters vol. 30, 2625 (1974).

*Primary Examiner*—Nicholas S. Rizzo
*Attorney, Agent, or Firm*—Steven R. Lammert; Everet F. Smith

[57] ABSTRACT

3-Halomethyl-3-cephems are provided by reacting a 3-methylenecepham with an alkali metal salt of a lower alcohol or a bicyclic amidine base in the presence of a positive halogenating agent at a temperature ranging from $-80°$ to about $20°$ C. The 3-halomethylcephems provided by this invention are useful intermediates for the preparation of known cephalosporin antibiotics.

31 Claims, No Drawings

PROCESS FOR PREPARATION OF 3-HALOMETHYLCEPHEMS

BACKGROUND OF THE INVENTION

This invention relates to the cephalosporin class of antibiotics. In particular, this invention relates to a process for preparing 3-halomethyl-3-cephem compounds from 3-methylenecephams.

3-Halomethylcephems are known in the cephalosporin art and have proved to be useful intermediates for the preparation, via nucleophilic displacement of the halogen atom, of many related cephalosporin antibiotic compounds. 3-Halomethylcephems have heretofore been available by allylic halogenation of the corresponding desacetoxycephalosporin compounds (U.S. Pat. Nos. 3,637,678 and 3,705,897) and by halogenation of the corresponding desacetylcephalosporins (U.S. Pat. No. 3,658,799). More recently 3-halomethylcephems have been prepared by cleavage of 3-acetoxymethyl and 3-carbamoyloxymethyl cephems with hydrohalic acids [S. Karady, T. Y. Cheng, S. H. Pines and M. Sletzinger, *Tetrahedron Letters*, 30, 2625 (1974)].

It is an object of this invention to provide a novel process for the preparation of 3-halomethylcephems from 3-methylenecephams.

SUMMARY OF THE INVENTION

This invention is directed to a process for preparing 3-halomethylcephems represented by the general formula

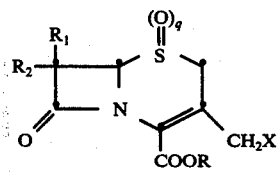

by reacting in an inert organic solvent a 3-methylenecepham of the formula

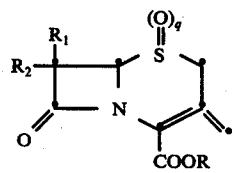

with an alkali metal salt of a $C_1$-$C_7$ alcohol or a bicyclic amidine base in the presence of a positive halogenating agent at sub-ambient temperatures, preferably between −80° and 0° C. wherein in the above formulae X is fluoro, chloro, bromo, or iodo; q is 1 or 0 representing a sulfoxide or sulfide respectively; R is a carboxylic acid protecting group, preferably one which can be readily removed so as to provide the carboxylic acid form of the 3-halomethylcephem or compounds derived therefrom; $R_1$ is hydrogen or methoxy; and $R_2$ is an imido group such as phthalimido or maleimido, or preferably an acylamino group, representing a wide variety of known penicillin and cephalosporin side chains including phenylacetamido, phenoxyacetamido, 2-thienylacetamido, phenylglycylamido, mandelamido, and like groups.

DETAILED DESCRIPTION OF THE INVENTION

This invention provides a process for preparing a 3-halomethylcephem compound of the formula

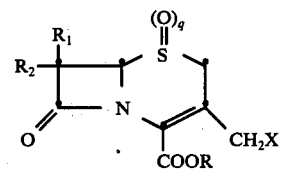

which comprises reacting a 3-methylenecepham of the formula

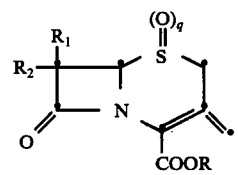

with from about 3 to about 6 equivalents of an alkali metal salt of a secondary $C_1$-$C_7$ alcohol or with from about 1 to about 3 equivalents of an alkali metal salt of a primary or tertiary $C_1$-$C_7$ alcohol or a bicyclic amidine base of the formula

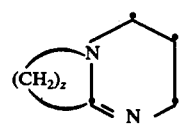

in the presence of about 1 to about 6 equivalents of a positive halogenating agent selected from the group consisting of tert-butyl hypochlorite, bromine, tert-butyl hypobromite, iodine monobromide, 1,5-diazabicyclo[5.4.0]-undec-5-ene (DBU) hydrobromide perbromide, iodine, iodine monochloride, tert-butyl hypoiodide and perchloryl fluoride in an inert organic solvent at a temperature of about −80° to about 20° C. wherein in the above formulae X is fluoro, chloro, bromo, or iodo;
z is 3, 4 or 5;
q is 1 or 0;
R is a carboxylic acid protecting group;
$R_1$ is hydrogen or methoxy;
$R_2$ is
(1) an imido group of the formula

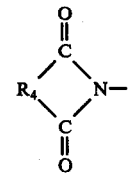

wherein $R_4$ is $C_2$-$C_4$ alkenylene, 1,2-phenylene, or 1,2-cyclohexenylene;
(2) an amido group of the formula

wherein R₃ is (a) hydrogen, $C_1$-$C_3$ alkyl, halomethyl, 3-(2-chlorophenyl)-5-methylisoxazol-4-yl or 4-protected amino-4-protected carboxybutyl (b) benzyloxy, 4-nitrobenzyloxy, 2,2,2-trichloroethoxy, tert-butoxy, or 4-methoxybenzyloxy;

(c) the group —R″ wherein R″ is 1,4-cyclohexadienyl, phenyl or phenyl substituted with 1 or 2 substituents independently selected from the group consisting of halo, protected hydroxy, nitro, cyano, trifluoromethyl, $C_1$-$C_3$ alkyl, and $C_1$-$C_7$ alkoxy;

(d) an arylalkyl group of the formula

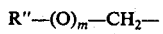

wherein R″ is as defined above, and m is 0 or 1;

(e) a substituted arylalkyl group of the formula

wherein R‴ is R″ as defined above, 2-thienyl or 3-thienyl, and W is protected hydroxy or protected amino; or (f) a heteroarylmethyl group of the formula

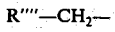

wherein R″″ is 2-thienyl, 3-thienyl, 2-furyl, 2-thiazolyl, 5-tetrazolyl, 1-tetrazolyl, or R₂ is (3) an imidazolidinyl group of the formula

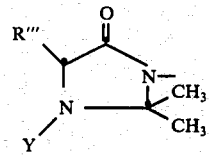

wherein R‴ is as defined above and Y is acetyl or nitroso;
with the limitations that when a $C_1$-$C_7$ primary alkoxide base is employed in conjunction with tert-butyl hypochlorite, R₁ is methoxy; and when a brominating agent is employed and R‴ of R″″ is 2-thienyl, 3-thienyl or 2-furyl, additionally, a halogen quenching agent is added to the reaction mixture.

In the foregoing definition of the process of the present invention the term "$C_1$-$C_3$ alkyl" refers to methyl, ethyl, n-propyl or isopropyl. The term "$C_1$-$C_7$ alkoxy" refers to such groups as methoxy, ethoxy, n-propoxy, isopropoxy, n-butoxy, tert-butoxy, cyclohexyloxy, benzyloxy and like groups. Illustrative of an "alkali metal salt of a primary $C_1$-$C_7$ alcohol" are lithium methoxide, sodium ethoxide, potassium ethoxide, lithium butoxide, sodium benzyloxide, and sodium n-propoxide. Representative of an "alkali metal salt of a secondary $C_1$-$C_7$ alcohol" are sodium isopropoxide, lithium sec-butoxide, sodium cyclohexyloxide, and potassium cyclohexyloxide. Illustrative of an "alkali metal salt of a tertiary $C_1$-$C_7$ alcohol" are potassium tert-butoxide, sodium 1-methylcyclohexyloxide, potassium 2-methyl-2-butoxide and lithium tert-butoxide.

Exemplary of "halomethyl" groups are fluoromethyl, chloromethyl, bromomethyl, or iodomethyl. Imido groups represented when R₄ is $C_2$-$C_4$ alkylene are maleimido, 3-ethylmaleimido, 3,4-dimethylmaleimido and like imido groups. Imido groups represented when R₄ is 1,2-cyclohexenylene or 1,2-phenylene are 2,3,5,6-tetrahydrophthalimido or phthalimido respectively.

When in the above definition R″ represents a substituted phenyl group, R″ can be a mono or disubstituted halophenyl group such as 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a protected hydroxy phenyl group such as 4-benzyloxyphenyl, 3-benzyloxyphenyl, 4-tert-butoxyphenyl, 4-tetrahydropyranyloxyphenyl, 4-(4-nitrobenzyloxy)phenyl, 2-phenacyloxyphenyl, 4-benzhydryloxyphenyl, 4-trityloxyphenyl and like groups; a nitrophenyl group such as 3-nitrophenyl or 4-nitrophenyl; a cyanophenyl group, for example, 4-cyanophenyl; a mono or dialkyl substituted phenyl group such as 4-methylphenyl, 2,4-dimethylphenyl, 2-ethylphenyl, 4-isopropylphenyl, 4-ethylphenyl, 3-n-propylphenyl and the like; a mono or di-alkoxyphenyl group, for example, 2,6-dimethoxyphenyl, 4-methoxyphenyl, 3-ethoxyphenyl, 4-isopropoxyphenyl, 4-tert-butoxyphenyl, 3-ethoxy-4-methoxyphenyl and the like. Also, R″ represents disubstituted phenyl groups wherein the substituents can be different for example, 3-methyl-4-methoxyphenyl, 3-chloro-4-benzyloxyphenyl, 2-methoxy-4-bromophenyl, 4-ethyl-2-methoxyphenyl, 3-chloro-4-nitrophenyl, 2-methyl-4-chlorophenyl and like disubstituted phenyl groups bearing different substituents.

The term "protected amino" as employed in the above definition has reference to an amino group substituted with one of the commonly employed amino blocking groups such as the tert-butoxycarbonyl group (t-BOC); the benzyloxycarbonyl group, the 4-methoxybenzyloxycarbonyl group, the 4-nitrobenzyloxycarbonyl group, or the 2,2,2-trichloroethoxycarbonyl group. Like conventional amino protecting groups such as those described by J. W. Barton in "Protective Groups in Organic Chemistry," J. F. W. McOmie, Ed., Plenum Press, New York, N.Y., 1973, Chapter 2 shall be recognized as suitable.

The term "protected hydroxy" has reference to the readily cleavable groups formed with an hydroxyl group such as the formyloxy group, the chloroacetoxy group, the benzyloxy group, the benzhydryloxy group, the trityloxy group, the 4-nitrobenzyloxy group, the trimethylsilyloxy group, the phenacyloxy group, the tert-butoxy group, the methoxymethoxy group, the tetrahydropyranyloxy group, and the like. Other hydroxy protecting groups, including those described by C. B. Reese in "Protective Groups in Organic Chemistry", supra, Chapter 3 shall be considered as within the term "protected hydroxy" as used herein.

The term "protected carboxy" has reference to a carboxy group which has been protected by one of the commonly used carboxylic acid protecting groups employed to block or protect the carboxylic acid functionality while reactions involving other functional sites of the compound are carried out. Such protected carboxy groups are noted for their ease of cleavage by hydrolytic or by hydrogenolytic methods to the corresponding carboxylic acid. Examples of carboxylic acid ester protecting groups include methyl, tert-butyl, benzyl, 4-methoxybenzyl, $C_2$-$C_6$ alkanoyloxymethyl, 2-iodoethyl, 4-nitrobenzyl, diphenylmethyl (benzhydryl), phenacyl, p-halophenacyl, 2,2,2-trichloroethyl, succinimidomethyl, tri($C_1$-$C_3$ alkyl)silyl and like ester forming moieties. Other known conventional carboxy protecting groups such as those described by E. Haslam in "Protective Groups in Organic Chemistry", supra, Chapter 5, shall be recognized as suitable. The nature of such ester forming groups is not critical so long as the particular ester formed therewith is stable under the reaction conditions described hereinafter. Preferred carboxylic acid ester protecting groups are tert-butyl, 4-methoxybenzyl, benzhydryl, 4-nitrobenzyl, and 2,2,2-trichloroethyl.

In the foregoing definitions, hydroxy, amino, and carboxy protecting groups are not exhaustively defined. The function of such groups is to protect the reactive functional groups during the preparation of the desired products and then be removed without disrupting the remainder of the molecule. Many such protective groups are well known in the art and the use of other groups equally applicable to the process and compounds of the present invention shall be recognized as suitable. Thus, there is no novelty or inventiveness asserted with regard to the "protecting groups" alluded to in this specification, nor it is intended that the invention be limited by the groups specifically disclosed herein.

Likewise the nature of the side chain group $R_2$ is not critical to the process of the present invention, that is, the process of converting a 3-methylenecepham to a 3-halomethylcephem. It should be noted, however, that some side chain groups, notably those containing a thienyl or furyl moiety, are particularly susceptible to halogenation on the heteroaryl group under reaction conditions within the scope of the present invention. As detailed hereinbelow, however, special precautions, including the use of halogen quenching agents preferably in conjunction with lower reaction temperatures, can be employed to minimize the possibility of concomitant side chain halogenation during the conversion to which the present process is directed. Since the side chains on the product of the process of this invention and on compounds derived therefrom are often subsequently cleaved, and the resulting nucleus esters then reacylated, possible side chain halogenation does not affect the utility of the process of this invention.

Representative of the acylamino group,

as defined hereinabove are formamido, acetamido, propionamido, butyramido, 2-pentenoylamino, chloroacetamido, bromoacetamido, 5-tert-butoxycarbonylamino-5-tert-butoxycarbonylvaleramido, and the like.

Illustrative of the particular acylamino group,

are benzamido, 2,6-dimethoxybenzamido, 4-chlorobenzamido, 4-methylbenzamido, 3,4-dichlorobenzamido, 4-cyanobenzamido, 3-bromobenzamido, 3-nitrobenzamido and the like.

Exemplary of the acylamino group

when $R_3$ is a group of the formula $R''(O)_m CH_2$— and $m$ is 0, are cyclohexa-1,4-dienylacetamido, phenylacetamido, 4-chlorophenylacetamido, 3-methoxyphenylacetamido, 3-cyanophenylacetamido, 3-methylphenylacetamido, 4-bromophenylacetamido, 4-ethoxyphenylacetamido, 4-nitrophenylacetamido, 3,4-dimethoxyphenylacetamido and the like; and when $m$ is 1, representative acylamino groups are phenoxyacetamido, 4-cyanophenoxyacetamido, 4-chlorophenoxyacetamido, 3,4-dichlorophenoxyacetamido, 2-chlorophenoxyacetamido, 4-methoxyphenoxyacetamido, 2-ethoxyphenoxyacetamido, 3,4-dimethylphenoxyacetamido, 4-isopropylphenoxyacetamido, 3-cyanophenoxyacetamido, 3-nitrophenoxyacetamido and like substituted phenoxyacetamido groups.

Illustrative of the acylamino groups when $R_3$ is a substituted arylalkyl group of the formula

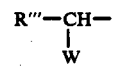

and when W is protected hydroxy are 2-formyloxy-2-phenylacetamido, 2-benzyloxy-2-(4-methoxyphenyl)acetamido, 2-(4-nitrobenzyloxy)-2-(3-chlorophenyl)acetamido, 2-chloroacetoxy-2-(4-methoxyphenyl)acetamido, 2-benzyloxy-2-phenylacetamido, 2-trimethylsilyloxy-2-(4-chlorophenyl)acetamido, 2-benzhydryloxy-2-phenylacetamido and like groups. Representative of such groups when W is protected amino are 2-(4-nitrobenzyloxycarbonylamino)-2-(2-thienyl)acetamido, 2-(2,2,2-trichloroethoxycarbonylamino)-2-phenylacetamido, 2-chloroacetamido-2-(1,4-cyclohexadien-1-yl)acetamido, 2-(4-methoxybenzyloxycarbonylamino)-2-(4-methoxyphenyl)-acetamido, 2-benzhydryloxycarbonylamino-2-(3-thienyl)acetamido, 2-(1-carbomethoxy-2-propenyl)amino-2-phenylacetamido, and like groups.

Exemplary of the acylamino group

when $R_3$ is a heteroarylmethyl group of the formula $R''''$—$CH_2$— are 2-thienylacetamido, 3-thienylacetmido, 2-furylacetmido, a 2-thiazolylacetamido group of the formula

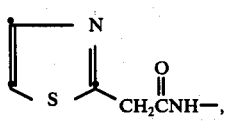

a 1-tetrazolylacetamido group of the formula

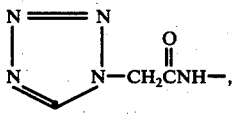

a 5-tetrazolylacetamido group of the formula

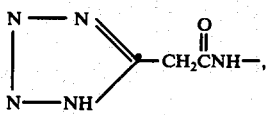

or a 3-(2-chlorophenyl)-5-methylisoxazol-4-ylamido group of the formula

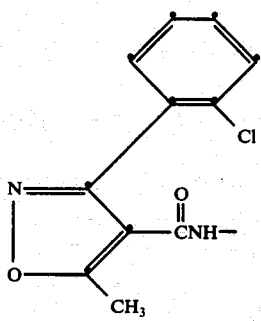

Representative of $R_1$ when $R_1$ is an imidazolidinyl group of the formula

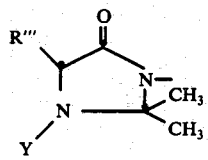

are the 2,2-dimethyl-3-nitroso-5-oxo-4-phenyl-1-imidazolidinyl group, the 2,2-dimethyl-3-nitroso-5-oxo-4-(4-benzyloxyphenyl)-1-imidazolidinyl group, the 2,2-dimethyl-3-acetyl-5-oxo-4-(1,4-cyclohexadien-1-yl)-1-imidazolidinyl group, the 2,2-dimethyl-3-nitroso-5-oxo-4-(2-thienyl)-1-imidazolidinyl group and like substituted imidazolidinyl groups.

Preferred acylamino groups include formamido, acetamido, 4-nitrobenzyloxycarbonylamino, phenoxyacetamido, phenylacetamido and 2-thienylacetamido. Phenylacetamido and phenoxyacetamido are most preferred.

The starting materials for the process of the present invention, 3-exomethylenecephams, were first disclosed as a generic class in U.S. Pat. No. 3,275,626. 7-Amino and 7-acylamino 3-exomethylenecephams can be prepared by the electroreduction (pH 2-7) of the corresponding cephalosporin compounds having a 3-substituted methyl group such as acyloxymethyl, acylthiomethyl or quaternary ammonium methyl (U.S. Pat. No. 3,792,995). Alternatively the exomethylenecepham starting materials for the present invention can be prepared in accordance with the procedure of R. R. Chauvette and P. A. Pennington in the *Journal of Organic Chemistry*, 38, 2994 (1973) in which 3-methylenecephams are prepared from cephalosporanic acids by first treating the cephalosporanic acids with selected sulfur nucleophiles such as thiourea, thiobenzoic acid, potassium ethyl xanthate or sodium thiosulfate and then reducing the respective product, $C_3$-(substituted)thiomethyl cephem derivatives, with either Raney nickel in aqueous ethanol or zinc in formic acid-dimethylformamide. Cephalosporanic acid derivatives have also been converted to 3-exomethylenecephams on treatment with chromium (II) salts in aqueous media [M. Ochiai et al., *J. Chem. Soc. Chemical Communications*, 800 (1972)]. The 3-exomethylene cepham sulfoxide starting materials for the process of the present invention are prepared by oxidation of the corresponding sulfides with an equivalent amount of metachloroperbenzoic acid. 3-Exomethylenecephams having a 7-methoxy group may be prepared from the corresponding 7-methoxycephalosporanic acids by procedures identical to those described in the references cited herein-above for the preparation of unsubstituted 3-exomethylenecepham compounds.

The products of the process of this invention are 3-halomethylcephems. The term "halomethyl" refers to chloromethyl, bromomethyl, iodomethyl or fluoromethyl. Whether the products are chloro, bromo, iodo or fluoro derivatives is determined by the respective nature of the particular positive halogenating agent employed in the process. Positive halogenating agents suitable for the process of this invention are as follows: tert-butyl hypochlorite, providing 3-chloromethylcephems; bromine, 1,5-diazabicyclo [5.4.0]undec-5-ene (DBU) hydrobromide perbromide, iodine monobromide, and tert-butyl hypobromite providing 3-bromomethylcephems; iodine, iodine monochloride and tert-butyl hypoiodite providing 3-iodomethylcephems, and perchloryl fluoride providing 3-fluoromethylcephems.

Although the manner in which the reactants for the process of this invention are combined is not critical, it is most preferred that the base is not contacted with the exomethylenecepham starting material without the halogenating agent being present. It should be noted, however, that the bases employed in the process of this invention will react with the exomethylenecepham in the absence of halogenating agents, at varying rates depending on the reaction temperature, to provide desacetoxymethylcephalosporins. Such conversions have been reported in the chemical literature [R. R. Chauvette and P. A. Pennington, *Journal of Organic Chemistry*, 38, 2994 (1973)]. If the base and the exomethylenecepham are combined, it is therefore preferred that the halogenating agent be present in the mixture or that it be added immediately thereafter. The conversion of 3-exomethylenecephams to 3-halomethylcephems is typically carried out by adding a solution of the substrate 3-exomethylenecepham to a stirred solution of a bicyclic amidine base or an alkali metal salt of a $C_1$-$C_7$ alcohol and the positive halogenating agent in an inert organic solvent.

Any of a wide variety of inert organic solvents may be employed as the medium for the halogenation process of this invention. By "inert organic solvent" is meant an organic solvent which, under the conditions of the process, does not enter into any appreciable reaction with either the reactants or the products. A dry aprotic organic solvent is preferred. Trace amounts of water such as that found in commercially dried solvents, can be tolerated; however, it is generally preferred that the process of this invention, be carried out under anhydrous conditions. Suitable solvents include, for example, aromatic hydrocarbons such as benzene, chlorobenzene, toluene, ethylbenzene, xylene and the like; halogenated aliphatic hydrocarbons such as chloroform, methylene chloride, carbon tetrachloride, 1,2-dichloroethane (ethylene chloride), 1,1,2-trichloroethane, 1,1-dibromo-2-chloroethane, and the like; aliphatic nitriles such as acetonitrile or propionitrile; esters such as ethyl acetate, butyl acetate, and the like; ethers such as 1,4-dioxane, tetrahydrofuran, diethyl ether, dimethoxyethane and the like; amides such as N,N-dimethylformamide, N,N-dimethylacetamide or hexamethylphosphoric triamide (HMPA); and any other appropriate aprotic solvents. Preferred solvents or solvent mixtures are those having a freezing point below about −10° C. Highly preferred solvents for the process of the present invention are methylene chloride, chloroform, 1,2-dichloroethane and tetrahydrofuran. Tetrahydrofuran is most preferred.

Suitable bases which can be employed to effectuate the halogenation of the process of this invention include bicyclic amidine bases and alkali metal salts of $C_1$-$C_7$ alcohols. The bicyclic amidine bases are represented by the general formula

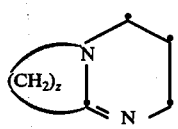

wherein Z is an integer from 3 to 5. Exemplary of such bases are 1,4-diazabicyclo[4.3.0]non-5-ene (DBN) and 1,5-diazabicyclo[5.4.0]undec-5-ene(DBU); both are commercially available. The term "alkali metal salts of $C_1$-$C_7$ alcohols" includes the sodium, potassium, and lithium salts of primary, secondary and tertiary $C_1$-$C_7$ alcohols such as methanol, ethanol, isopropanol, sec-butanol, tert-butanol, n-propanol, cyclohexanol, benzyl alcohol, n-hexanol and like alcohols. Exemplary of such alkoxide bases suitable for the process of this invention are lithium methoxide, sodium methoxide, potassium ethoxide, sodium benzyloxide, potassium tert-butoxide, lithium isopropoxide, sodium n-propoxide, sodium cyclohexyloxide and like sodium, lithium and potassium salts. The preferred of the aforementioned bases to be employed in the process of this invention are bicyclic amidine bases and lithium salts of secondary alcohols; 1,5-diazabicyclo[5.4.0]undec-5-ene (DBU) and lithium isopropoxide are most preferred.

It should be noted that when the $C_7$ substituent, $R_1$ in the above formula, on the exomethylenecepham starting material is hydrogen and an alkali metal salt of a $C_1$-$C_7$ primary alcohol is employed as the base in the present process, the halogenating agent must be other than tert-butyl hypochlorite. If tert-butyl hypochlorite is employed in conjunction with a primary alkoxide base, concomitant C-7 alkoxylation will be effected along with the desired C-3' halogenation. Thus when, for example, DBU or potassium tert-butoxide is employed as the base and tert-butyl hypochlorite is employed as the halogenating agent only C-3' chlorination is effected. If, however, lithium methoxide is used instead of DBU or potassium tert-butoxide, C-3' chlorination and C-7 methoxylation will take place simultaneously, yielding a 7-methoxy-3-chloromethylcepham.

In carrying out the process of the present invention wherein a 3-exomethylenecepham is converted to a 3-halomethylcepham, the exomethylenecepham is reacted with from about 3 to about 6 equivalents of a secondary $C_1$-$C_7$ alcohol or with from about 1 to about 3 equivalents of an alkali metal salt of a primary or tertiary $C_1$-$C_7$ alcohol or a bicyclic amidine base per equivalent of exomethylenecepham in the presence of about 1 to about 6 equivalents of a positive halogenating agent. Generally when a primary or tertiary alkoxide or a bicyclic amidine base is employed, the conversion is carried out using about 2 to about 3 equivalents of base and about 3 to about 4 equivalents of halogenating agent; preferably the reaction is carried out using about 3 equivalents of base and about 3 equivalents of halogenating agent for each equivalent of 3-exomethylenecepham starting material. When, however, a secondary alkoxide base is employed, the conversion is typically effected using about 4 to about 6 equivalents of base and halogenating agent for each equivalent of exomethylenecepham starting material; the use of about 6 equivalents of each is preferred. It should be noted that as the amount of halogenating agent is decreased below about 2.5 equivalents per equivalent of exomethylenecepham, an increased amount of the corresponding desacetoxycephalosporin is found in the reaction products.

When an alkali metal salt of a $C_1$-$C_7$ alcohol is employed as the base in the present process, preferably an excess of a protic acid is added to the reaction mixture before it is allowed to warm above about 0° C. This optional but preferred procedure serves to preclude any undesirable side reactions between the 3-halomethylcepham product and the excess base in the reaction mixture. Both organic and inorganic protic acids are suitable. Representative of such are formic acid, acetic acid, propionic acid, trifluoroacetic acid, methanesulfonic acid, p-toluenesulfonic acid, hydrochloric acid, sulfuric acid and like organic and inorganic protic acids.

The process of the present invention is carried out at a temperature ranging from about −80° C. to about 20° C. Preferably the process is carried out between −80° C. and about 0° C. Generally, a reaction temperature of about −10° to about −40° is most preferred; however, where the side chain moiety of the cepham substrate is also subject to halogenation, especially bromination, the process of this invention is preferably carried out at a temperature of less than about −40°. Such halogen-reactive C-7 side chains include 2-thienylacetamido, 3-thienylacetamido, 2-furylacetamido and like groups.

In addition to preferably performing the process of this invention at lower temperature when the starting material has such halogen-reactive substituents, it is necessary when the halogenating agent is a brominating agent that a halogen quenching agent also be added to the reaction mixture. The halogen quenching agent is added to destroy any excess halogenating reagent thereby eliminating or substantially decreasing the likelihood of undesirable side reactions between any excess halogenating agent and halogen-reactive side chains present on the starting materials and the product 3-halomethylcephems.

The term "halogen quenching agent" as employed hereinabove in describing the process of this invention refers to those reagents not reactive with the cephem starting materials nor the cephem products of the process of this invention, but capable of reacting with the halogenating reagent, thereby rendering the halogenating reagent or more accurately any excess thereof unreactive toward the 3-halomethylcepham products of the process of this invention. Typically halogen quenching agents employed in the process of this invention are halogen reducing agents, however, other quenching agents with which the excess halogenating agent will react preferentially (versus further reaction with the 3-halocephem products) are suitable. Suitable halogen quenching agents include di($C_1$-$C_6$alkyl)sulfides, tri($C_1$-$C_6$alkyl)phosphites, olefins, acetylenes, and like organic halogen reactive agents. Likewise aqueous solutions of known reducing-inorganic salts such as bisulfite, metabisulfite, thiosulfate and dithionite salts can be successfully employed.

Exemplary of sulfide and phosphite halogen quenching agents useful in the process of the present invention are dimethylsulfide, di-n-propylsulfide, dicyclohexylsulfide, methylethylsulfide, trimethylphosphite, triethylphosphite, and tri-n-butylphosphite. Representative of the olefins and acetylenes which can be employed as quenching agents in the process of this invention are diethylacetylene dicarboxylate; vinylethers including methylvinylether, ethyl vinylether and like alkylvinyl ethers; and vinylesters like vinyl acetate. Exemplary of suitable reducing inorganic salts are sodium bisulfite, potassium bisulfite, sodium metabilsulfite, potassium thiosulfate, sodium dithionite and like reducing salts.

The halogen quenching salts are typically added to the reaction mixture after the halogenation reaction has reached completion, as detected, for example by comparative thin-layer chromatography, and preferably before the reaction mixture is allowed to warm above about 0° C. When aqueous solutions of the aforedescribed reducing inorganic salts are employed as quenching agents, their addition typically constitutes the first step in the work-up of the reaction mixture. However, where the reaction temperature is less than about −20° C., the aforedescribed organic halogen quenching agents may be added to the reaction mixture before the halogenation reaction is initiated. Thus, for example, 4'-methoxybenzyl 7-(2-thienylacetamido)-3-bromomethyl-3-cephem-4-carboxylate can be prepared by adding a solution of 1 equivalent from 4'-methoxybenzyl 7-(2-thienylacetamido)-3-methylenecepham-4-carboxylate in tetrahydrofuran to a solution of 3 equivalents of DBU, 3 equivalents of bromine, and 5 equivalents of trimethylphosphite in tetrahydrofuran at −40° C. The trimethylphosphite is unreactive to the halogenating agent at the lower reaction temperature, but as the reaction mixture is allowed to warm above the reaction temperature after the halogenation is complete, the trimethylphosphite only then reacts with the excess bromine in the mixture.

The major product of the aforedescribed example performed without the presence of a halogen quenching agent is 4'-methoxybenzyl 7-[2-(5-bromothienyl)acetamido]-3-bromomethyl-3-cephem-4-carboxylate. It should be noted that although side chain halogenation is generally undesirable, the 3-halomethylcephem products produced in such reactions are none the less useful in preparing other 3-halomethylcephem compounds. Thus, for example, the 4'-methoxybenzyl 7-[2-(5-bromothienyl)acetamido]-3-bromomethyl-3-cephem-4-carboxylate can be cleaved under conventional side chain cleavage conditions (PCl$_5$, pyridine/methanol) to provide the corresponding nucleus ester 4'-methoxybenzyl 7-amino-3-bromomethyl-3-cephem-4-carboxylate which thereafter can be reacylated as desired. Therefore, conversions of 3-methylenecephams to 3-halomethylcephems having, in addition, halogen substituted side chains, are also to be considered within the scope of the present invention.

The amount of quenching agent employed is not critical so long as a sufficient quantity is added to render inactive the excess halogenating agent in the reaction mixture. Generally, a 1–10 fold excess or more of the halogen quenching agent is employed.

Although the use of halogen quenching agents in the process of the present invention have been found necessary only in the instances where both a brominating agent is employed and the substrate exomethylenecepham has a halogenreactive side chain, higher yields of product 3-halomethylcephems are generally obtained when such quenching agents are employed. Typically, therefore, halogen quenching agents are employed in the process of the present invention, even where the substrate exomethylenecepham does not have a halogen-reactive side chain. The general use of halogen quenching agents in the process of this invention is therefore preferred.

The time of reaction will range generally from about 2 minutes to about 1 hour with the reaction time being dependent to some extent upon the particular reactants, the solvents employed, and the temperature at which the reaction is carried out. Usually the reaction will be complete after the reactants have been maintained in contact at the preferred temperatures for about 5 to 15 minutes. The reaction mixture can easily be monitored, for example, by comparative thinlayer chromatography, to determine when the halogenation reaction has reached completion.

Exemplary of the conversions effectuated by employing the process of the present invention are the following:

tert-butyl 7-phenylacetamido-3-methylenecepham-4-carboxylate to tert-butyl 7-phenylacetamido-3-bromomethyl-3-cephem-4-carboxylate using DBN and tert-butyl hypobromite;

benzyl 7-(4-nitrobenzyloxycarbonylamino)-3-methylenecepham-4-carboxylate to benzyl 7-(4-nitrobenzyloxycarbonylamino)-3-chloromethyl-4-carboxylate using potassium tertbutoxide and tert-butyl hypochlorite;

4'-nitrobenzyl 7-acetamido-3-methylenecepham-4-carboxylate to 4'-nitrobenzyl 7-acetamido-3-iodomethyl-3-cephem-4-carboxylate using iodine and DBU;

2',2',2'-trichloroethyl 7-(2-phenyl-2-benzyloxyacetamido)-3-methylenecepham-4-carboxylate to 2',2',2'-trichloroethyl-7-(2-phenyl-2-benzyloxyacetamido)-3-iodomethyl-3-cephem-4-carboxylate using iodine and sodium methoxide;

benzhydryl 7-formamido-3-methylenecepham-4-carboxylate 1-oxide to benzyhydryl 7-formamido-3-bromomethyl-3-cephem-4-carboxylate 1-oxide using DBU hydrobromide perbromide and DBU;

2'-iodoethyl 7-(2-formyloxy-2-phenylacetamido)-3-methylenecepham-4-carboxylate to 2'-iodoethyl 7-(2-formyloxy-2-phenylacetamido)-3-fluoromethyl-3-cephem-4-carboxylate using perchloryl fluoride and DBN;

4'-methoxybenzyl 7-phenoxyacetamido-7-methoxy-3-methylenecepham-4-carboxylate to 4'-methoxybenzyl 7-phenoxyacetamido-7-methoxy-3-bromomethyl-3-cephem-4-carboxylate using lithium cyclohexyloxide and bromine;

benzhydryl 7-(2,2-dimethyl-3-nitroso-5-oxo-4-phenyl-1-imidazolinyl)-3-methylenecepham-4-carboxylate to benzhydryl 7-(2,2-dimethyl-3-nitroso-5-oxo-4-phenyl-1-imidazolinyl)-3-chloromethyl-3-cephem-4-carboxylate using DBU and tert-butyl hypochlorite;

2',2',2'-trichloroethyl 7-[2-(4-nitrobenzyloxycarbonylamino)-2-phenylacetamido]-3-methylenecepham-4-carboxylate to 2',2',2'-trichloroethyl 7-[2-(4-nitrobenzyloxycarbonylamino)-2-phenylacetamido]-3-fluoromethyl-3-cephem-4-carboxylate using DBU and perchloryl fluoride;

4'-nitrobenzyl 7-(2-furylacetamido)-3-methylenecepham-4-carboxylate to 4'-nitrobenzyl 7-

(5bromo-2-furylacetamido)-3-bromomethyl-3-cephem-4-carboxylate using iodine monobromide and DBN;

tert-butyl 7-(4-chlorophenylacetamido)-3-methylenecepham-4-carboxylate 1-oxide to tert-butyl 7-(4-chlorophenylacetamido)-3-bromomethyl-3-cephem-4-carboxylate 1-oxide using lithium ethoxide and bromine; and 4'-methoxybenzyl 7-chloroacetamido-7-methoxy-3-methylenecepham-4-carboxylate to 4'-methoxybenzyl 7-chloroacetamido-7-methoxy 3-iodomethyl-3-cephem-4-carboxylate using DBU and iodine.

The products produced in accordance with the process of this invention can be isolated and purified by employing conventional experimental techniques. These include chromatographic separation, filtration, crystallization and recrystallization.

The product 3-halomethylcephem compounds of the process of this invention are useful as intermediates in the preparation of antibiotics. The sulfoxides can be reduced by known procedures, typically with phosphorous tribromide or phosphorous trichloride in dimethylformamide to provide the corresponding 3-halomethylcephems. The 3-halomethylcephem esters are converted to active antibiotics by cleavage of the ester function (U.S. Pat. No. 3,658,799). De-esterification can be achieved, depending on the nature of the ester group, by any one of several recognized procedures, including (1) treatment with an acid such as trifluoroacetic acid, formic acid, hydrochloric acid or the like; (2) treatment with zinc and an acid such as formic acid, acetic acid or hydrochloric acid; or (3) hydrogenation in the presence of palladium, platinum, rhodium, or a compound thereof, in suspension, or on a carrier such as barium sulfate, carbon, or alumina.

Alternatively the 3-halomethylcephems can be converted to other 3-(substituted)methylcephem compounds by nucleophilic displacement of the halo moiety. Such is a procedure recognized by those skilled in the art for preparing a wide variety of known active 3-heteroarylthiomethyl cephem compounds.

The following examples are provided to further illustrate the present invention. It is not intended that this invention be limited in scope by reason of any of these examples. In the following examples nuclear magnetic resonance spectra were obtained an a Varian Associates T-60 Spectrometer using tetramethylsilane as the reference standard. The chemical shifts are expressed in $\delta$ values in parts per million (ppm) and coupling constants (J) are expressed in cycles per second.

EXAMPLE 1

4'-Nitrobenzyl 7-phenoxyacetamido-3-bromomethyl-3-cephem-4-carboxylate

A. To a solution of 248 mg. of DBN and 20 ml. of tetrahydrofuran at $-78°$ C. was added 0.109 ml. of bromine. Immediately thereafter a solution of 0.483 g. of 4'-nitrobenzyl 7-phenoxyacetamido-3-methylenecepham-4-carboxylate in 15 ml. of tetrahydrofuran was added. The reaction mixture was stirred for 10 minutes at $-78°$ and then warmed to 0° at which temperature the mixture was stirred for 10 minutes. Then 0.118 ml. of trimethylphosphite was added. The reaction mixture was evaporated in vacuo to dryness to provide a red-brown foam which was then dissolved in methylene chloride, washed successively with 5% hydrochloric acid and saturated sodium chloride solution, dried over anhydrous magnesium sulfate and evaporated in vacuo to dryness to provide 536 mg. (95%) of the title product as a pink foam: nmr (CDCl$_3$) $\delta$3.6 (bs, 2, C$_2$—H), 4.46 (bs, 2, C$_3$—CH$_2$Br), 4.58 (s, 2, side chain CH$_2$), 5.05 (d, 1, J = 5 Hz, C$_6$—H), 5.40 (s, 2, ester CH$_2$), 5.95 (q, 1, J = 5 and 9 Hz, C$_7$—H) and 6.8–8.3 (ArH).

B. To a solution of 0.336 g. of potassium t-butoxide in tetrahydrofuran at $-80°$ C. was added in 0.12 ml. of bromine. A solution of 0.483 g. of 4'-nitrobenzyl 7-phenoxyacetamido-3-methylenecepham-4-carboxylate in 4 ml. of THF was then added. The reaction mixture was allowed to warm to 0° at which temperature the solution was stirred for 10 minutes before 10 drops of trimethylphosphite was added. The reaction mixture was evaporated in vacuo to dryness to provide a residue which was then taken up in methylene chloride and washed successively with 5% hydrochloric acid and twice with brine, dried over anhydrous magnesium sulfate, and evaporated in vacuo to dryness. The product thereby obtained was purified by preparative thin-layer chromatography to provide 0.50 g. of the title product. The nmr of the product thus obtained was identical to the nmr of that product obtained in part A immediately hereinabove.

C. The same procedure was followed as in part A above except the reaction was carried out on an 80 mm. scale using DBU as the base. To a solution of 36.48 g of DBU in 820 ml. of tetrahydrofuran at $-80°$ C. was added 14.4 ml. of bromine and subsequently a solution of 38.64 g. of 4'-nitrobenzyl 7-phenoxyacetamido-3-methylenecepham-4-carboxylate in 160 ml. of tetrahydrofuran. After 10 minutes at $-80°$ C. 14.4 ml. of trimethylphosphite was added dropwise over a 6 minute period. The reaction was then allowed to warm to 0° C. An additional 60 ml. of trimethylphosphite was then added to the mixture. The reaction mixture was then evaporated in vacuo to near dryness and the residue dissolved in methylene chloride. The methylene chloride solution was washed successively with 5% hydrochloric acid solution and saturated sodium chloride solution and then poured through a filter of silica gel and charcoal. The filtrate was then evaporated in vacuo to dryness to provide 35.6 g. (80%) of the title product.

D. To a solution of 0.456 g. of DBU in 15 ml of THF at $-80°$ was added 0.18 ml of bromine. Thereafter a solution of 0.483 g. of 4'-nitrobenzyl 7-phenoxyacetamido-3-methylenecepham-4-carboxylate in 4 ml of THF was added. The reaction mixture was allowed to warm to 0° at which temperature it was stirred for 10 minutes. The reaction mixture was then filtered through Merck silica gel using ethyl acetate as the eluant. The combined eluates were evaporated in vacuo to dryness to provide the title product as indicated by nmr.

EXAMPLE 2

4'-Nitrobenzyl 7-phenoxyacetamido-3-bromomethyl-3-cephem-4-carboxylate

A. To a solution of 2.28 g. of DBU in 50 ml. of tetrahydrofuran at $-20°$ C. was added 0.82 ml of bromine followed immediately by a solution of 2.415 g. of 4'-nitrobenzyl 7-phenoxyacetamido-3-methylenecepham-4-carboxylate in 20 ml. of tetrahydrofuran. The reaction mixture was allowed to stir for 30 minutes at $-20°$ to $-15°$ C. Then 50 ml. of methylene chloride and 150 ml. of aqueous sodium meta-bisulfite solution was added. The organic layer was separated, washed twice with sodium bisulfite solution. Evaporation in vacuo to dryness provided 2.90 g. of product which was dissolved in 75 ml. of methylene chloride. The resulting solution was washed 3 times with saturated sodium chloride/5% HCl solution, dried over anhydrous MgSO$_4$ and evaporated in vacuo to dryness. The product thereby obtained was slurried in 50 ml. of diethyl ether for 2 hours. Filtration provided 1.71 g. (60.8%) of the title product.

B. The same procedure was followed as described in Example 2A except sodium bisulfite was used instead of sodium meta-bisulfite. The title product was isolated in 59.4% yield.

EXAMPLE 3

4'-Nitrobenzyl 7-phenoxyacetamido 3-bromomethyl-3-cephem-4-carboxylate

To a solution of 0.228 g. of DBU in 20 ml. of methylene chloride at −78° C (dry ice/acetone) was added 0.082 ml. of bromine followed immediately by the addition of a solution of 0.241 g. of 4'-nitrobenzyl 7-phenoxyacetamido-3-methylenecepham-4-carboxylate in 15 ml. of methylene chloride. The reaction mixture was stirred for 10 minutes at −78° and then warmed to 0° C. at which temperature it was stirred for an additional 10 to 15 minutes. Dimethylsulfide (0.07ml.) was then added to the reaction mixture. The reaction mixture was evaporated in vacuo to dryness, and the residue thereby obtained was dissolved in methylene chloride. The methylene chloride solution was washed with 5% hydrochloric acid/saturated sodium chloride solution, dried over anhydrous magnesium sulfate, and evaporated in vacuo to dryness to provide a brown froth. Comparative thin-layer chromatography and nmr data indicate that the title product is the major constituent.

B. The same procedure was followed as described in (A) immediately hereinabove except that toluene was employed as the solvent instead of methylene chloride. Thin-layer chromatography and nmr data confirms the conversion to the title product.

C. Again the same general procedure was followed as described in (A) above with the following exceptions: 1,1,2-trichloroethane was employed as the solvent instead of methylene chloride; a liquid nitrogen/acetonitrile bath (−41° C.) was used instead of a dry ice acetone bath to prevent the solvent from freezing; and trimethylphosphite was employed instead of dimethylsulfide as the quenching agent. Thin-layer chromatography and nmr data indicate a 40% conversion to the title product.

D. The same procedure was followed as described in (A) above except that methanol was employed as the reaction medium instead of methylene chloride and trimethylphosphite was used as the quenching agent instead of dimethylsulfite. Thin-layer chromatography of the crude product is indicative of the desired conversion to the title product.

E. The same general procedure was followed as described in (A) above with the following exceptions: hexamethylenephoramide was employed as the reaction solvent instead of methylene chloride; a liquid nitrogen/acetonitrile bath (−41° C.) was used instead of a dry ice acetone bath; and trimethylphosphite was employed as the quenching agent instead of dimethylsulfide. Thin-layer chromatography shows a 50% conversion to the title product.

F. The same procedure was followed as described in (A) hereinabove with the following exceptions: 1,4-dioxane was employed as the reaction solvent instead of methylene chloride; an ice bath was used instead of a dry ice acetone bath to prevent the solvent from freezing; and trimethylphosphite was used as the quenching agent instead of dimethylsulfide. Thin-layer chromatography indicates a 75% conversion to the title product.

G. The same general procedure was followed as described in example (A) hereinabove with the following exceptions: 1,2-dimethoxyethane was used as the reaction solvent instead of methylene chloride; a liquid nitrogen/acetonitrile bath (−41° C.) was used instead of a dry ice acetone bath to prevent the solvent from freezing; and trimethylphosphite was used as a quenching agent instead of dimethylsulfide. Thin-layer chromatography indicates a clean and complete conversion to the title product.

H. The same procedure was followed as described in (A) hereinabove except that dimethylformamide was used as the reaction medium instead of methylene chloride and trimethylphosphite was used as the quenching agent instead of dimethylsulfide. Thin-layer chromatography of the final crude product indicates conversion to the title compound.

EXAMPLE 4

4'-Nitrobenzyl 7-phenoxyacetamido-3-bromomethyl-3-cephem-4-carboxylate

To a solution of 64 mg. of methanol in 20 ml. of tetrahydrofuran (THF) at −80° C. was added 1.15 ml. of a 1.75 M. solution of methyl lithium. After 5 minutes 0.11 ml. of bromine was added to the resulting THF solution of lithium methoxide. A solution of 0.483 g. of 4'-nitrobenzyl 7-phenoxyacetamido-3-methylenecepham-4-carboxylate in 4 ml. of tetrahydrofuran was then added dropwise. Following the completion of the addition of the THF solution of the methylenecepham substrate the mixture was allowed to stir for 5 minutes at −80° and then was allowed to warm to 0° C. After 10 minutes at 0° 4 drops of trimethylphosphite was added. Subsequently, the reaction mixture was evaporated in vacuo to dryness and the residue thereby obtained was taken up in methylene chloride. The solution thereby obtained was washed successively with 5% HCl solution, water, and saturated sodium chloride solution. The organic layer was then separated, dried over anhydrous sodium sulfate and evaporated in vacuo to dryness. The product thereby obtained was then purified by preparative thin-layer chromatography employing silica gel plates developed with a 7:3 benzene/ethyl acetate solution. A total of 126 mg. of the title product was isolated. The nmr spectrum of the isolated product was identical to that of the product prepared in Example 1.

EXAMPLE 5

4'-Nitrobenzyl 7-phenoxyacetamido-3-bromomethyl-3-cephem-4-carboxylate 1-oxide To a solution of 0.912 g. of DBU in 15 ml. of tetrahydrofuran at −80° was added 0.36 ml. of bromine. Thereafter a solution of 0.499 g. of 4'-nitrobenzyl 7-phenoxyacetamido-3-methylenecepham-4-carboxylate 1-oxide in 4 ml. of hexamethylphosphoramide. After 10 minutes 0.186 ml. of trimethylphosphite was added. The reaction mixture was then allowed to warm to 0° and after 5 minutes an additional 2 ml. of trimethylphosphite was added. The reaction mixture was thereafter evaporated in vacuo to dryness and the residue thereby obtained was dissolved in methylene chloride. The methylene chloride solution was washed successively with 5% hydrochloric acid, water, and twice with saturated sodium chloride solution, dried over anhydrous sodium sulfate and evaporated in vacuo to dryness to provide a product which was purified by preparative thin-layer chromatography; 60 mg. of the title product was isolated: nmr (DMSO$_{d-6}$) δ3.96 (bs, 2, C$_2$—H), 4.57 (s, 2, C$_3$—C$\underline{H}_2$Br), 4.73 (s, 2, side chain CH$_2$), 5.09 (d, 1, J = 5 Hz, C$_6$—C$\underline{H}$), 5.50 (s, 2, ester CH$_2$), 6.10 (q, 1, J = 10 and 5 Hz, C$_7$—H) and 6.9–8.2 (ArH).

EXAMPLE 6

4'-Nitrobenzyl 7-(2-thienylacetamido)-3-bromomethyl-3-cephem-4-carboxylate

To a solution of 9.12 g. of DBU in 200 ml. of dry tetrahydrofuran at −78° (dry ice/acetone) was added 3.5 ml. of bromine. The resulting mixture was allowed to stir at −78° C. for 10 minutes. To this mixture was added a solution of 9.46 g. of 4'-nitrobenzyl 7-(2-thienylacetamido)-3-methylenecepham-4-carboxylate in 100 ml. of THF dropwise over 5 minutes. After the addition of the substrate solution was complete, the mixture was allowed to stir at 10 minutes at −78° C. The dry ice/acetone bath was then removed and replaced with an ice water bath, and the mixture was allowed to stir for 6 minutes, after which time 5.0 ml. of trimethylphosphite was added. The mixture was allowed to stir for 10 minutes and then was evaporated in vacuo to dryness to provide a dark colored residue. The residue was taken up in methylene chloride, and the resulting solution was washed successively with water, 5% hydrochloric acid, and brine, and then dried over anhydrous sodium sulfate. Approximately 10 g. of Darco G-60 was then added. The solution was then filtered and the resulting yellow orange-colored filtrate was evaporated in vacuo to dryness. The residue thereby obtained was recrystallized from methylene chloride/hexane to provide 6.96 g. (63%) of the title product: nmr (DMSO$_{d-6}$) δ 3.80 (bs, 4, side chain CH$_2$ + C$_2$—H), 4.55 (bs, 2, —C$\underline{H}_2$Br), 5.20 (d, 1, J = 4.5 Hz, C$_6$—H), 5.82 (dd, 1, J = 4.5 and 9Hz, C$_7$—H) and 6.9–8.4 (ArH).

EXAMPLE 7

Benzhydryl 7-(2-thienylacetamido)-3-bromomethyl-3-cephem-4-carboxylate

Benzhydryl 7-(2-thienylacetamido)-3-methylenecepham-4-carboxylate was converted to the title product in accordance with the procedure described in Example 6. nmr (CDCl$_3$) δ 3.50 (bs, 2, C$_2$—H), 3.84 (s, 2, side chain CH$_2$), 4.30 (s, 2, C$_3$—C$\underline{H}_2$Br), 4.98 (d, 1, J = 4.5, C$_6$—H), 5.86 (q, 1, J = 4.5 and 9 Hz, C$_7$—H), 6.84 (d, 1, J = 9 Hz, side chain NH) and 7.0–7.6 (ArH).

EXAMPLE 8

4'-Nitrobenzyl 7-(2-thienylacetamido)-3-bromomethyl-3-cephem-4-carboxylate (DBU hydrobromide per bromide)

DBU hydrobromide per bromide was prepared as follows: To a solution of 20.3 g. of DBU and 100 ml. of 48% hydrobromic acid at −5° was added 32.06 g. of bromine dropwise over 10 minutes. The orange precipitate which formed was separated, washed with acetic acid and water, and dissolved in methylene chloride. The methylene chloride solution was washed with water, and then dried over anhydrous sodium sulfate. Ethyl acetate was then added to the methylene chloride solution with cooling until crystallization was initiated. After allowing the solution to stand at 0° for 2 hours, the title product was separated by filtration and washed with ethyl acetate and ether. Yield: 22.6 g.; m.p. 119°–122° C. The filtrate from above was concentrated and with cooling gave an additional 9.5 g. of the title product as orange crystals (m.p. 118°–121° C). Total Yield: 32.1 g. (61%). To a solution of 2.35 g. of DBU hydrobromide per bromide and 0.34 g. DBU in 20 ml. of tetrahydrofuran at room temperature was added 0.946 g. of 4'-nitrobenzyl 7-(2-thienylacetamido)-3-methylenecepham-4-carboxylate and 20 ml. of THF. The solution immediately darkened. After 2 minutes 0.5 ml. of trimethylphosphite was added, and the reaction mixture was then immediately evaporated in vacuo to dryness. The residue thereby obtained was dissolved in methylene chloride and the resulting solution was washed with 5% hydrochloric acid solution and saturated sodium chloride solution, dried over anhydrous sodium sulfate and then evaporated in vacuo to dryness. The residue crystallized from methylene chloride/ethanol to give 0.92 g. of the title product as pink crystals. The structure of the product was confirmed by nmr and TLC data.

EXAMPLE 9

4'-Nitrobenzyl 7-[2-(5-bromothienylacetamido)]-3-bromomethyl-3-cephem-4-carboxylate To a solution of 4.56 g. of DBU and 50 ml. of THF at −78° C. was added 1.8 ml. of bromine. After the mixture was stirred for 15 minutes at −78° C. a solution of 4.73 g. of 4'-nitrobenzyl 7-(2-thienylacetamido)-3-methylenecepham-4-carboxylate in 40 ml. of THF was added. The mixture was allowed to warm to −15° over a 30 minute period. To the reaction mixture was then added 250 ml. of water and 150 ml. of methylene chloride. The organic layer was separated, washed with 5% hydrochloric acid and water, and dried over anhydrous sodium sulfate. The methylene chloride solution was then filtered through 150 g. of silica gel eluding with methylene chloride. The eluant containing the major reaction product was evaporated in vacuo to dryness. The residue thereby obtained was crystallized from methylene chloride/hexane to give the title product as pale yellow crystals; m.p. 144°–146° (Decomp): λ$_{max.}^{EtOH}$ 260 mμ (19,600); nmr (DMSO$_{d-6}$) δ6.79 and 7.05 (d's, 1 each, J = 3.5 Hz, thiophene C$_3$ and C$_4$-protons).

Analysis Calcd. for C$_{21}$H$_{17}$N$_3$O$_6$S$_2$Br$_2$:
C, 39.01; H, 2.63; N, 6.50; Br, 24.76. Found: C, 40.22; H, 2.57; N, 6.59; Br, 24.37.

EXAMPLE 10

4'-Nitrobenzyl 7-phenoxyacetamido-3-chloromethyl-3-cephem-4-carboxylate

To a solution of 0.312 g. of DBU in 15 ml. of tetrahydrofuran at −80° C. was added 0.286 ml. of tertbutyl hypochlorite. A solution of 0.483 g. of 4'-nitrobenzyl 7-phenoxyacetamido-3-methylenecepham-4-carboxylate in 4 ml. of THF was then added to the cold (−80° C.) mixture. After stirring the reaction mixture at −80° for 10 minutes, 10 drops of trimethylphosphite were added. The reaction mixture was allowed to warm to 0° and then was evaporated in vacuo to dryness. The residue was dissolved in methylene chloride, and the resulting solution was washed with 5% HCl solution and saturated sodium chloride solution, separated, dried over anhydrous sodium sulfate, and evaporated in vacuo to dryness to provide 260 mg. of the title product:

nmr (CDCl$_3$) δ3.60 (bs, 2, C$_2$—H), 4.58 (s, 4, C$_3$—CH$_2$Cl + side chain CH$_2$), 5.03 (d, 1, J = 5 Hz, C$_6$—H), 5.38 (s, 2, ester CH$_2$), 5.93 (q, 1, J = 5 and 9Hz, C$_7$—H), and 6.8–8.4 (ArH).

EXAMPLE 11

4'-Nitrobenzyl 7-phenoxyacetamido-3-fluoromethyl-3-cephem-4-carboxylate

To a solution of 0.483 g. of p-nitrobenzyl 7-phenoxyacetamido-3-methylenecepham-4-carboxylate in 30 ml. of dry THF at −78° C. under a dry nitrogen atmosphere was added 25 ml. of a dry saturated solution of perchloryl fluoride in dimethylformamide (4.7 g. FClO$_3$/liter at 25° C.) prepared by bubbling perchloryl fluoride gas into dimethylformamide at room temperature for 10 minutes. To the resulting solution of the substrate methylene cepham and perchloryl fluoride at −78° C. was added a solution of 0.153 g. of 1,5-diazabicyclo [5.4.0]undec-5-ene (DBU) in 5 ml. of dry tetrahydrofuran dropwise over a period of 5 minutes. When the addition of the DBU solution was complete, the mixture was stirred 3 minutes at −78° C., after which time 0.118 g. of trimethylphosphite was added. The reaction mixture was then evaporated in vacuo to near dryness. The residue thereby obtained was dissolved in methylene chloride, and the solution was washed successively with 1N.HCl, water, and twice with saturated sodium chloride solution. The washed methylene chloride solution was then dried over anhydrous sodium sulfate and thereafter evaporated in vacuo to dryness to yield 443 mg. of a colorless foam. After a preliminary purification by high-pressure liquid chromatography the product was finally purified by preparative thin-layer chromatography using a 7:3 benzene/ethyl acetate solution to develop the silica gel preparative TLC plates. Extraction of the appropriate band with methylene chloride provided 21.1 mg. of the title product as a colorless resin: nmr (CDCl$_3$) δ 3.56 (bs, 2, C$_2$—H), 4.55 (s, 2, side chain CH$_2$), 5.0 (d, 1, J = 5 Hz, C$_6$—H), 5.35 (d, ABq's, 2, J$_F$ = 47 Hz, C$_3$—CH$_2$F), 5.32 (s, 2, ester CH$_2$), 5.91 (q, 1, J = 5 and 9 Hz, C$_7$—H) and 6.7–8.2 (ArH);

fluorine magnetic resonance (CDCl$_3$) triplet, J$_H$ = 47 Hz.

EXAMPLE 12

Benzhydryl 7-(2-thienylacetamido)-3-fluoromethyl-3-cephem-4-carboxylate

The title product was prepared from benzhydryl 7-(2-thienylacetamido)-3-methylenecepham-4-carboxylate in accordance with the procedures described by Example 11.

nmr (CDCl$_3$) δ3.44 (s, 2, C$_2$—H), 3.80 (s, 2, side chain CH$_2$), 4.89 (d, 1, J = 5 Hz, C$_6$—H), 4.84 and 5.64 (2bs's, 1 each, J$_F$ = 48 Hz, C$_3$—CH$_2$F), 5.86 (q, 1, J = 5 and 9 Hz), 6.65 (d, 1, J = 9 Hz, side chain NH) and 6.8–7.5 (ArH).

EXAMPLE 13

4'-Nitrobenzyl 7-phenoxyacetamido-3-iodomethyl-3-cephem-4-carboxylate

To a solution of 0.456 g. of DBU in 15 ml. of tetrahydrofuran at −80° was added 0.84 g. of iodine in 4 ml. of THF and thereafter dropwise a solution of 0.483 g. of p-nitrobenzyl 7-phenoxyacetamido-3-methylenecepham-4-carboxylate in 4 ml. of tetrahydrofuran. After 5 minutes at −80° C, 0.983 ml. of trimethylphosphite was added and the reaction mixture was then allowed to warm to 0° C. After about 10 minutes an additional 1 ml. of trimethylphosphite was added. The reaction mixture was then evaporated in vacuo to dryness. The residue thereby obtained was dissolved in methylene chloride and washed successively with 5% HCl, water, and twice with saturated sodium chloride solution. The methylene chloride solution was then dried over anhydrous sodium sulfate and then evaporated in vacuo to dryness to provide an impure product which was chromatographed on a silica gel column to provide 260 mg. of the title product:

nmr (CDCl$_3$) 3.44 and 3.82 (ABq, 2, J = 18Hz, C$_2$—H), 4.40 (s, 2, C$_3$—CH$_2$I), 4.54 (s, 2, side chain CH$_2$), 4.98 (d, 1, J = 5 Hz, C$_6$—H), 5.34 (s, 2, ester CH$_2$), 5.82 (q, 1, J = 5 and 9 Hz, C$_7$—H) and 6.8–8.4 (ArH).

EXAMPLE 14

4'-Nitrobenzyl 7-phenoxyacetamido-3-chloromethyl-3-cephem-4-carboxylate

To a solution of 0.12 g. of isopropanol in 20 ml. of THF at 0° C. was added 1.1 ml. of 1.84 M. methyl lithium in THF. After the resulting solution was cooled to −80° C., 0.286 ml. of tert-butyl hypochlorite and a solution of 0.483 g. of 4-nitrobenzyl 7-phenoxyacetamido-3-methylenecepham-4-carboxylate in 4 ml. of THF were added successively. The reaction mixture was then allowed to warm to 0° C. After 10 minutes at 0° C., 1 ml. of acetic acid and 1 ml. of trimethylphosphite were added. The mixture was then evaporated in vacuo to dryness to provide a residue which was dissolved in methylene chloride and washed with aqueous sodium bicarbonate solution. The methylene chloride solution was then dried and evaporated in vacuo to dryness. The product thereby obtained was purified by preparative thick layer chromatography (silica gel plates/benzene-ethyl acetate gradient) to provide 100 mg. of the title product:

nmr (CDCl$_3$) δ 3.63 (br. s, 2, C$_2$—H), 4.58 (s, 4, C$_3$'—H and side chain CH$_2$), 5.05 (d, 1, J = 5 Hz, C$_6$—H), 5.38 (s, 2, ester CH$_2$), 5.94 (dd, 1, J = 5 and 9 Hz) and 6.8–8.4 (m, 9, ArH).

EXAMPLE 15

4'-Nitrobenzyl 7-phenoxyacetamido-3-bromomethyl-3-cephem-4-carboxylate

To a solution of 0.360 g. of isopropanol in 25 ml. of THF at 9° was added 3.26 ml. of 1.84 M. methyl lithium in THF. After the mixture was cooled to −80° C., 0.36 ml. of bromine and a solution of 0.483 g. of 4'-nitrobenzyl 7-phenoxyacetamido-3-methylenecepham-4-carboxylate in 4 ml. of THF were added successively. The reaction mixture was then allowed to warm to 0° C. After 10 minutes, 1 ml. of acetic acid and 2 ml. of trimethylphosphite were added. Evaporation in vacuo to dryness provided a product which was dissolved in methylene chloride and washed successively with aqueous sodium bicarbonate solution and 5% hydrochloric acid. The solution was then filtered through Merck silica gel. The filtrate was evaporated in vacuo to dryness to give 0.374 g. (67%) of the title product.

I claim:

1. A process for preparing a 3-halomethylcephem compound of the formula

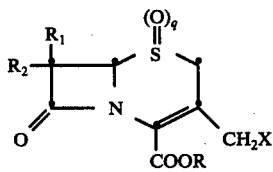

which comprises reacting a 3-methylenecepham of the formula

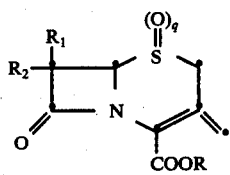

with from about 3 to about 6 equivalents of an alkali metal salt of a secondary $C_1$-$C_7$ alcohol or with from about 1 to about 3 equivalents of an alkali metal salt of a primary or tertiary $C_1$-$C_7$ alcohol or a bicyclic amidine base of the formula

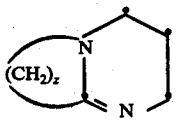

in the presence of about 1 to about 6 equivalents of a positive halogenating agent selected from the group consisting of tert-butyl hypochlorite, bromine, tert-butyl hypobromite, idoine monobromide, 1,5-diazabicyclo[5.4.0]undec-5-ene (DBU) hydrobromide perbromide, iodine, iodine monochloride, tert-butyl hypoiodite and perchloryl fluoride in an inert organic solvent at a temperature of about −80° to about 20° C. wherein in the above formulae $X$ is fluoro, chloro, bromo or iodo;
$z$ is 3, 4, or 5;
$q$ is 1 or 0;
$R$ is a carboxylic acid protecting group;
$R_1$ is hydrogen or methoxy;
$R_2$ is
1. an imido group of the formula

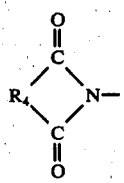

wherein $R_4$ is $C_2$-$C_4$ alkenylene, 1,2-phenylene, or 1,2-cyclohexenylene;
2. an amido group of the formula

wherein $R_3$ is
a. hydrogen, $C_1$-$C_3$ alkyl, halomethyl, 3-(2-chlorophenyl)-5-methylisoxazol-4-yl or 4-protected amino-4-protected carboxybutyl;
b. benzyloxy, 4-nitrobenzyloxy, 2,2,2-trichloroethoxy, tert-butoxy, or 4-methoxybenzyloxy;
c. the group —R″ wherein R″ is 1,4-cyclohexadienyl, phenyl or phenyl substituted with 1 or 2 substituents independently selected from the group consisting of halo, protected hydroxy, nitro, cyano, trifluoromethyl, $C_1$-$C_3$ alkyl, and $C_1$-$C_7$ alkoxy;
d. an arylalkyl group of the formula

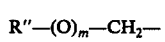

wherein R″ is as defined above, and $m$ is 0 or 1;
e. a substituted arylalkyl group of the formula

wherein R‴ is R″ as defined above, 2-thienyl or 3-thienyl, and W is protected hydroxy or protected amino; or
f. a heteroarylmethyl group of the formula

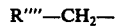

wherein R″″ is 2-thienyl, 3-thienyl, 2-furyl, 2-thiazolyl, 5-tetrazolyl, 1-tetrazolyl; or $R_2$ is
3. an imidazolidinyl group of the formula

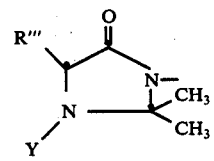

wherein R‴ is as defined above and Y is acetyl or nitroso;
with the limitations that when a $C_1$-$C_7$ primary alkoxide base is employed in conjunction with tert-butyl hypochlorite, $R_1$ is methoxy; and when a brominating agent is employed and R‴ or R″″ is 2-thienyl, 3-thienyl or 2-furyl, additionally, a halogen quenching agent is added to the reaction mixture.

2. The process of claim 1 wherein R is methyl, tert-butyl, benzyl, 4-methoxybenzyl, $C_2$-$C_6$ alkanoyloxymethyl, 2-iodoethyl, 4-nitrobenzyl, benzhydryl, phenacyl, p-halophenacyl, 2,2,2-trichloroethyl, tri($C_1$-$C_3$ alkyl)silyl nd succinimidomethyl.

3. The process of claim 1 wherein $q = 0$.

4. The process of claim 1 wherein the base is a bicyclic amidine base.

5. The process of claim 4 wherein the base is 1,5-diazabicyclo[5.4.0]undec-5-ene (DBU) or 1,4-diazabicyclo[4.3.0]non-5-ene (DBN).

6. The process of claim 1 wherein the base is an alkali metal salt of a $C_1$-$C_7$ alcohol.

7. The process of claim 6 wherein, additionally, before the reaction mixture is allowed to warm above about 0°, an excess of a protic acid is added to the reaction mixture.

8. The process of claim 6 wherein the base is an alkali metal salt of a secondary $C_1$-$C_7$ alcohol.

9. The process of claim 8 wherein the base is a lithium salt of a $C_1$-$C_7$ secondary alcohol.

10. The process of claim 9 wherein the base is lithium isopropoxide.

11. The process of claim 1 wherein $R_2$ is an amido group of the formula

12. The process of claim 11 wherein $R_2$ is formamido, acetamido, 4-nitrobenzyloxycarbonylamino, phenylacetamido, phenoxyacetamido and 2-thienylacetamido.

13. The process of claim 1 wherein the reaction medium is methylene chloride, chloroform, 1,2-dichloroethane, or tetrahydrofuran.

14. The process of claim 1 wherein the halogen quenching agent is a di($C_1$-$C_6$ alkyl)sulfide, a tri($C_1$-$C_6$ alkyl)phosphite, diethylacetylene dicarboxylate, methylvinylether, ethylvinylether, vinylacetate or a bisulfite, metabisulfite, thiosulfate or dithionite salt.

15. The process of claim 1 wherein R''' or R'''' is other than 2-thienyl, 3-thienyl or 2-furyl and wherein, additionally, a halogen quenching agent is added to the reaction mixture before the reaction mixture is allowed to warm above about 0° C.

16. The process of claim 15 wherein the halogen quenching agent is a halogen reducing agent.

17. The process of claim 15 wherein the halogen quenching agent is dimethyl sulfide, di-n-propyl sulfide, dicyclohexyl sulfide, methylethyl sulfide, trimethylphosphite, triethylphosphite or tri-n-butylphosphite.

18. The process of claim 15 wherein the halogen quenching agent is a water soluble bisulfite, metabisulfite, thiosulfate or dithionite inorganic salt.

19. The process of claim 1 wherein X is bromo, $R_1$ is hydrogen and wherein the exomethylenecepham starting material is added to a solution of about 3 equivalents of bromine and about 3 equivalents of DBU per equivalent of exomethylenecepham.

20. The process of claim 19 wherein $R_3$ is an arylalkyl group of the formula R''—(O)$_m$—CH$_2$—.

21. The process of claim 20 wherein the reaction is carried out in tetrahydrofuran.

22. The process of claim 21 wherein after the reaction is allowed to proceed for about 15 minutes, an aqueous solution of sodium bisulfite or sodium metabisulfite is added.

23. The process of claim 1 wherein X is bromo and $R_1$ is hydrogen and wherein the conversion is effected by employing about 6 equivalents of bromine and about 6 equivalents of lithium isopropoxide per equivalent of exomethylenecepham starting material.

24. The process of claim 23 wherein $R_3$ is an arylalkyl group of the formula R''—(O)$_m$—CH$_2$—.

25. The process of claim 24 wherein additionally before the reaction mixture is allowed to warm above about 0° C. an excess of both a protic acid and a halogen quenching agent is employed.

26. A process for preparing a 3-bromomethylcephem compound of the formula

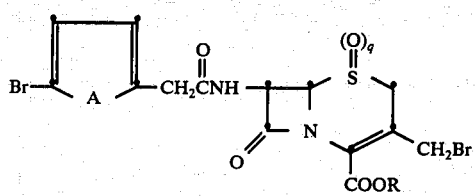

which comprises reacting a 3-methylenecepham of the formula

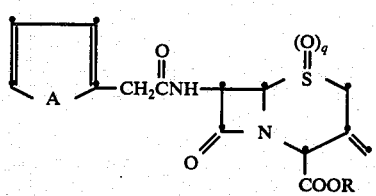

with from 1 to about 3 equivalents alkali metal salt of a $C_1$-$C_7$ alcohol or a bicyclic amidine base of the formula

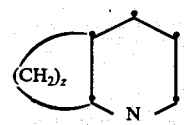

in the presence of about 2 to about 4 equivalents of a positive brominating agent selected from the group consisting of bromine, DBU perbromide hydrobromide, iodine monobromide and tert-butyl hypobromite in an inert organic solvent at a temperature from about −20° to 25° C wherein in the above formula z is 3, 4, or 5;
q is 1 or 0;
A is 0 or S; and
R is a carboxylic acid protecting group.

27. The process of claim 21 wherein R is methyl, tert-butyl, benzyl, 4-methoxybenzyl, $C_2$-$C_6$ alkanoyloxymethyl, 2-iodoethyl, 4-nitrobenzyl, benzhydryl, phenacyl, p-halophenacyl, 2,2,2-trichloroethyl, tri($C_1$-$C_3$ alkyl)silyl and succinimidomethyl.

28. The process of claim 22 wherein q is 0.

29. The process of claim 19 wherein $R_2$ is an amido group of the formula

wherein $R_3$ is a substituted arylalkyl group of the formula

30. The process of claim 29 wherein the reaction is carried out in tetrahydrofuran.

31. The process of claim 30 wherein after the reaction is allowed to proceed for about 15 minutes, an aqueous solution of sodium bisulfite or sodium metabisulfite is added.

* * * * *

UNITED STATES PATENT AND TRADEMARK OFFICE
CERTIFICATE OF CORRECTION

PATENT NO. : 4,042,585

DATED : August 16, 1977

INVENTOR(S) : Gary A. Koppel

It is certified that error appears in the above-identified patent and that said Letters Patent are hereby corrected as shown below:

Column 7, line 1,

" 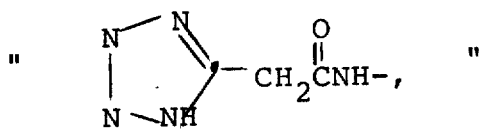 "

should read

-- 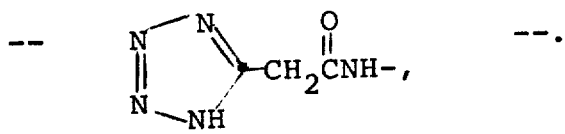 --.

Column 7, line 52, "quaternary" should read --quarternary--.

Column 12, line 3, "halogenreactive" should read --halogen-reactive--.

Column 12, line 20, "thinlayer" should read --thin-layer--.

Column 13, line 1, "(5bromo-2-furylacetamido)" should read --(5-bromo-2-furylacetamido)--.

Column 13, line 44, "obtained an" should read --obtained on--.

Column 18, line 63, "tertbutyl" should read --tert-butyl--.

UNITED STATES PATENT AND TRADEMARK OFFICE
CERTIFICATE OF CORRECTION

Page 2 of 2

PATENT NO. : 4,042,585
DATED : August 16, 1977
INVENTOR(S) : Gary A. Koppel

It is certified that error appears in the above-identified patent and that said Letters Patent are hereby corrected as shown below:

Column 24, line 25,

" 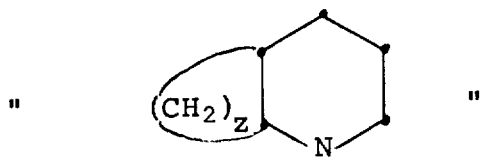 "

should read

-- 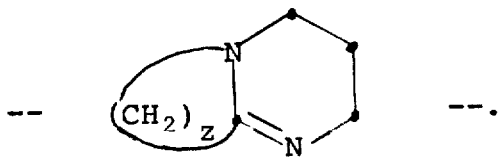 --.

Signed and Sealed this

Twenty-fourth Day of November 1981

[SEAL]

Attest:

Attesting Officer

GERALD J. MOSSINGHOFF

Commissioner of Patents and Trademarks